United States Patent
Irisawa et al.

(10) Patent No.: US 10,568,605 B2
(45) Date of Patent: Feb. 25, 2020

(54) ACOUSTIC IMAGE GENERATION APPARATUS AND PROGRESS DISPLAY METHOD IN GENERATING AN IMAGE USING THE APPARATUS

(71) Applicant: FUJIFILM Corporation, Tokyo (JP)

(72) Inventors: Kaku Irisawa, Ashigarakami-gun (JP); Takeya Abe, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1555 days.

(21) Appl. No.: 14/319,405

(22) Filed: Jun. 30, 2014

(65) Prior Publication Data
US 2014/0316270 A1 Oct. 23, 2014

Related U.S. Application Data

(63) Continuation of application No. PCT/JP2012/008354, filed on Dec. 27, 2012.

(30) Foreign Application Priority Data

Dec. 28, 2011 (JP) ................................ 2011-287562
Dec. 10, 2012 (JP) ................................ 2012-269400

(51) Int. Cl.
*A61B 8/00* (2006.01)
*A61B 5/00* (2006.01)
(52) U.S. Cl.
CPC .......... *A61B 8/4245* (2013.01); *A61B 5/0095* (2013.01); *A61B 8/54* (2013.01)
(58) Field of Classification Search
CPC ... A61B 8/4245; A61B 8/4254; A61B 5/0095; A61B 8/54
See application file for complete search history.

(56) References Cited

U.S. PATENT DOCUMENTS 5,645,066 A 7/1997 Gandini et al.
5,782,766 A * 7/1998 Weng ..................... G06T 7/246
128/916

(Continued)

FOREIGN PATENT DOCUMENTS

CN 102047140 A 5/2011
JP 9-299367 A 11/1997

(Continued)

OTHER PUBLICATIONS

Office Action issued in the corresponding Chinese Patent Application No. 201280065489.X, dated Jul. 28, 2015 with an English Translation.

(Continued)

*Primary Examiner* — James M Kish
(74) *Attorney, Agent, or Firm* — Birch, Stewart, Kolasch & Birch, LLP

(57) ABSTRACT

In an acoustic image generation apparatus with a probe having an ultrasonic transducer, providing a scanning length setting part that sets a target scanning length in a scanning process of the probe, a coordinate obtaining part that sequentially obtains a coordinate of the probe in real space, a scanned length calculation part that calculates a scanned length based on the coordinate obtained by the coordinate obtaining part, a progress level display generation part that generates a progress level display that indicates progress of the scanning process based on the target scanning length and the scanned length, and a display part that displays the progress level display.

11 Claims, 11 Drawing Sheets

(56) References Cited

U.S. PATENT DOCUMENTS

| | | | |
|---|---|---|---|
| 2002/0133098 A1* | 9/2002 | Shechtman | A61B 5/064 600/594 |
| 2004/0039312 A1* | 2/2004 | Hillstead | A61N 7/02 601/2 |
| 2005/0187471 A1* | 8/2005 | Kanayama | A61B 5/0091 600/437 |
| 2006/0058651 A1 | 3/2006 | Chiao et al. | |
| 2006/0184031 A1 | 8/2006 | Ichioka et al. | |
| 2007/0239004 A1 | 10/2007 | Kakee et al. | |
| 2011/0079083 A1* | 4/2011 | Yoo | G01S 7/52065 73/632 |

FOREIGN PATENT DOCUMENTS

| | | |
|---|---|---|
| JP | 10-43182 A | 2/1998 |
| JP | 10-262964 A | 10/1998 |
| JP | 2004-202260 A | 7/2004 |
| JP | 2006-51360 A | 9/2006 |
| JP | 2006-231035 A | 9/2006 |
| JP | 2008-86742 A | 4/2008 |
| JP | 2010-12295 A | 1/2010 |
| JP | 2011-521763 A | 7/2011 |
| WO | WO 2009/147621 A2 | 12/2009 |

OTHER PUBLICATIONS

Japanese Office Action, dated May 12, 2015, in related application No. JP2012-269400.

International Search Report, dated Apr. 16, 2013, issued in PCT/JP2012/008354.

\* cited by examiner

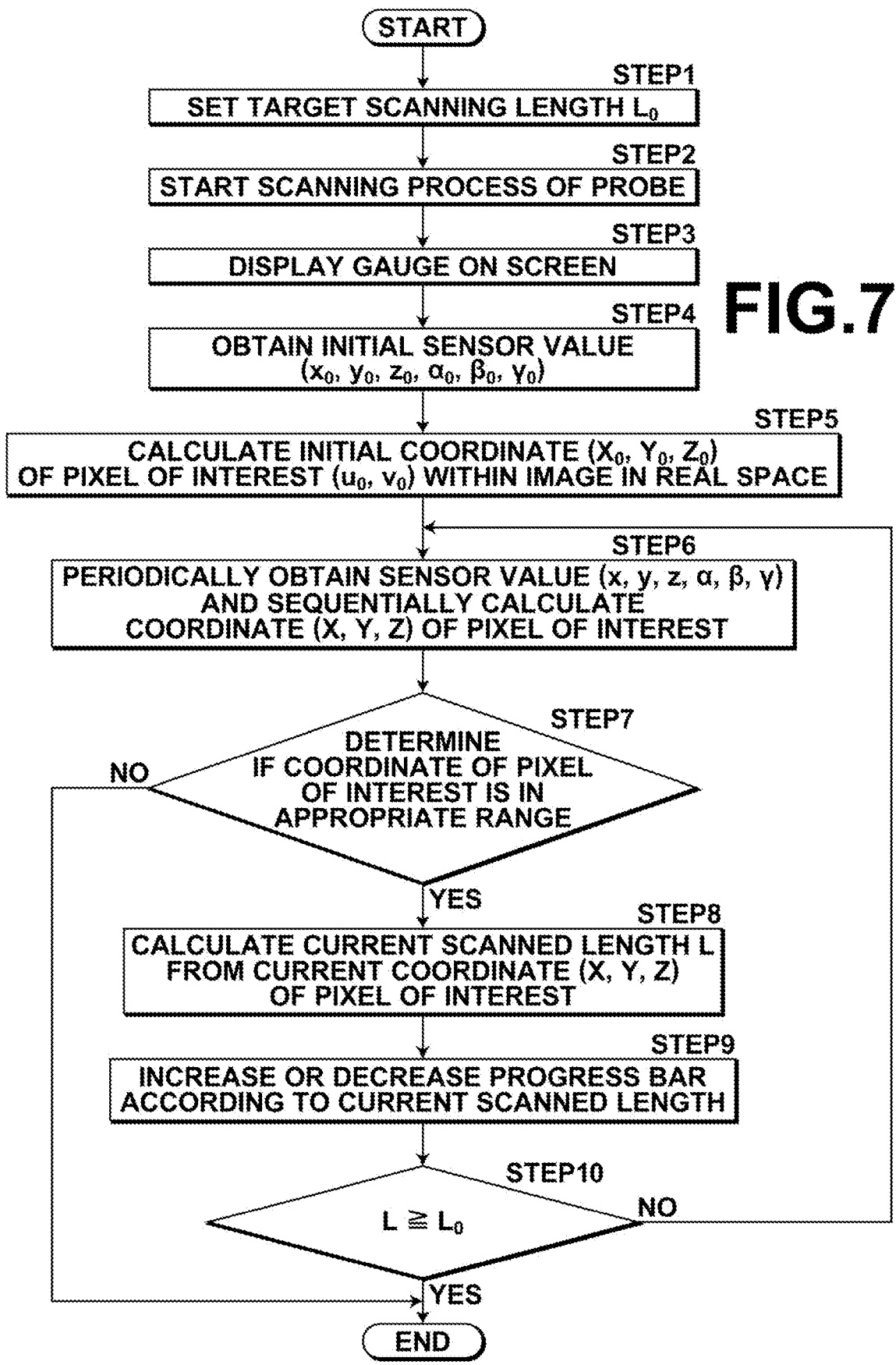

ACOUSTIC IMAGE GENERATION APPARATUS AND PROGRESS DISPLAY METHOD IN GENERATING AN IMAGE USING THE APPARATUS

CROSS-REFERENCE TO RELATED APPLICATIONS

This application is a Continuation of PCT International Application No. PCT/JP2012/008354 filed on Dec. 27, 2012 which claims priority under 35 U.S.C. § 119 (a) to Japanese Patent Application No. 2011-287562 filed on Dec. 28, 2011 and Japanese Patent Application No. 2012-269400 filed on Dec. 10, 2012, the contents of which are hereby expressly incorporated herein by reference in its entirety.

BACKGROUND OF THE INVENTION

Technical Field

The present invention relates to an acoustic image generation apparatus capable of generating tomographic images of ultrasonic images, photoacoustic images, and the like, and a progress display method in generating an image using the apparatus.

Description of the Related Art

Conventionally, ultrasonic imaging is known as a method for obtaining an internal tomographic image of a subject in which an ultrasonic image is generated by projecting an ultrasonic wave onto a subject and detecting an ultrasonic wave reflected from the inside of the subject and a morphological tomographic image of the inside of the subject is obtained. In the mean time, development of systems for displaying not only a morphological image but also a functional tomographic image has been in progress in recent years in the field of subject examination. As one of such systems, a system that uses photoacoustic spectroscopy is known. In the photoacoustic spectroscopy, pulsed light having a predetermined wavelength (e.g., the wavelength of visible light, near infrared light, or intermediate infrared light) is projected onto a subject and a photoacoustic wave which is an elastic wave generated in the subject as a result of absorption of energy of the pulsed light by a particular substance is detected and the density of the particular substance is quantitatively measured. The particular substance in the subject is, for example, glucose or hemoglobin in the blood, or the like. The technology in which a photoacoustic wave is detected and a photoacoustic image is generated based on the detected signal in the manner described above is called photoacoustic imaging (PAT) or photoacoustic tomography (PAT).

As for the devices that generate acoustic images (ultrasonic images and photoacoustic images), development of devices equipped with a handheld ultrasonic probe having an ultrasonic transducer (and further a light outputting means in the case of photoacoustic imaging, such as an optical fiber) is conducted widely as described, for example, in Japanese Unexamined Patent Publication Nos. 2004-202260 and 2010-012295.

For example, Japanese Unexamined Patent Publication No. 2004-202260 discloses a method in which three-dimensional ultrasonic image data are generated by detecting a state of motion of the probe when generating an ultrasonic image and obtaining an ultrasonic image signal at a predetermined interval based on the state of motion. This allows an ultrasonic image to be generated at regular intervals regardless of the scanning speed of the probe.

Further, for example, Japanese Unexamined Patent Publication No. 2010-012295 discloses a method in which pulsed laser light is guided to the distal end of the probe using a bundle fiber in which many thin silica optical fibers are bundled.

SUMMARY OF THE INVENTION

In the mean time, in generating a continuous acoustic image or a three-dimensional acoustic image, there may be a case in which a process of scanning the probe is required on a region for which an image is desired to be generated. In such a case, the conventional method has a problem that it is difficult for the user of the probe to understand the progress or the end point of the scanning process, i.e., it is difficult to understand until when (or to where) the probe needs to be scanned.

The present invention has been developed in view of the problem described above, and it is an object of the present invention to provide an acoustic image generation apparatus that facilitates, in generating an acoustic image by scanning a probe, confirmation of progress of the scanning process, and a display method of the progress.

In order to solve the problem described above, the acoustic image generation apparatus according to the present invention includes:

a probe having an acoustic detection element that detects an acoustic wave propagating in a subject;

an acoustic image generation means that generates, based on an acoustic signal of the acoustic wave detected by the probe, an acoustic image of the acoustic signal;

a scanning length setting means that sets a target scanning length in a scanning process of the probe;

a coordinate obtaining means that sequentially obtains a coordinate of the probe in real space;

a scanned length calculation means that calculates a scanned length based on the coordinate obtained by the coordinate obtaining means;

a progress level display generation means that generates a progress level display that indicates progress of the scanning process based on the target scanning length and the scanned length; and a display means that displays the progress level display.

The term "scanned length" as used herein refers to the distance from the position where scanning is started (scanning start point) to the current position of the probe.

In the acoustic image generation apparatus according to the present invention, it is preferable that the progress level display is a graph-like progress meter having an indicator that indicates the progress level.

Further, in the acoustic image generation apparatus according to the present invention, it is preferable that the progress meter has a scanning assist display that assists the scanning of the probe such that the scanning process is completed properly.

Still further, in the acoustic image generation apparatus according to the present invention, it is preferable that the scanning assist display includes an ideal speed display that guides the scanning of the probe such that the scanning speed of the probe becomes a predetermined value.

Further, in the acoustic image generation apparatus according to the present invention, it is preferable that the ideal speed display is a constant speed index that moves at a constant speed in the forward direction of the indicator.

Still further, in the acoustic image generation apparatus according to the present invention, it is preferable that, when the distance between a position indicated by the constant speed index and a position indicated by the indicator becomes greater than or equal to a predetermined value, the constant speed index resumes the movement from the position indicated by the indicator.

Alternatively, in the acoustic image generation apparatus according to the present invention, it is preferable that the scanning assist display includes a scanning limit display that guides the scanning of the probe such that the scanning speed of the probe falls within a predetermined range.

Further, in the acoustic image generation apparatus according to the present invention, it is preferable that the scanning limit display is an upper limit index that indicates a position corresponding to an upper limit value in variation of the coordinate of the probe in relation to the position indicated by the indicator.

Still further, in the acoustic image generation apparatus according to the present invention, it is preferable that the scanned length calculation means calculates a coordinate of a pixel included in an imaging area defined by the probe and located remote from the center axis of the probe in the real space based on the coordinate of the probe in the real space, and calculates the scanned length based on the coordinate of the pixel in the real space.

Further, it is preferable that the acoustic image generation apparatus according to the present invention includes a control means that terminates the acoustic image generation process when a variation in the scanned length becomes greater than or equal to a predetermined value.

Still further, in the acoustic image generation apparatus according to the present invention, it is preferable that the coordinate obtaining means is a magnetic sensor unit or an acceleration sensor unit.

Further, the acoustic image generation apparatus according to the present invention may be of a configuration in which:

the probe includes a light projection means that projects measuring light onto the subject, and detects a photoacoustic wave generated in the subject due to the projection of the measuring light; and the acoustic image generation means generates a photoacoustic image based on a photoacoustic signal of the photoacoustic wave.

Still further, the acoustic image generation apparatus according to the present invention may be of a configuration in which:

the probe detects a reflected acoustic wave of an acoustic wave transmitted to the subject; and the acoustic image generation means generates a reflected acoustic wave image based on a reflected acoustic wave signal of the reflected acoustic wave.

The progress display method according to the present invention includes, in a scanning process in which a probe having an acoustic detection element is scanned in generating an acoustic image, the steps of:

sequentially obtaining a coordinate of the probe in real space;

calculating a scanned length based on the sequentially obtained coordinate;

generating a progress level display that indicates progress of the scanning process based on a predetermined target scanning length and the scanned length; and displaying the progress level display.

In the progress display method according to the present invention, it is preferable that the progress level display is a graph-like progress meter having an indicator that indicates the progress level.

Further, in the progress display method according to the present invention, it is preferable that the progress meter has a scanning assist display that assists the scanning of the probe such that the scanning process is completed properly.

Still further, in the progress display method according to the present invention, it is preferable that the scanning assist display includes an ideal speed display that guides the scanning of the probe such that the scanning speed of the probe becomes a predetermined value.

Alternatively, in the progress display method according to the present invention, it is preferable that the scanning assist display includes a scanning limit display that guides the scanning of the probe such that the scanning speed of the probe falls within a predetermined range.

Further, in the progress display method according to the present invention, it is preferable that the scanned length is calculated by calculating a coordinate of a pixel included in an imaging area defined by the probe and located remote from the center axis of the probe in the real space based on the coordinate of the probe in the real space, and based on the coordinate of the pixel in the real space.

According to the acoustic image generation apparatus and the progress display method of the present invention, it is possible, in a scanning process in which a probe having an ultrasonic transducer is scanned in generating an acoustic image, to sequentially obtain a coordinate of the probe in real space, calculate a scanned length based on the sequentially obtained coordinate, and generate a progress level display that indicates progress of the scanning process based on the predetermined target scanning length and the scanned length. As a result, the user of the probe may visually confirm the progress, so that, in generating an acoustic image by scanning the probe, progress of the scanning process may be confirmed easily.

BRIEF DESCRIPTION OF THE DRAWINGS

FIG. 7 is a flowchart illustrating scanning process steps of the probe.

BEST MODE FOR CARRYING OUT THE INVENTION

Figure 1:
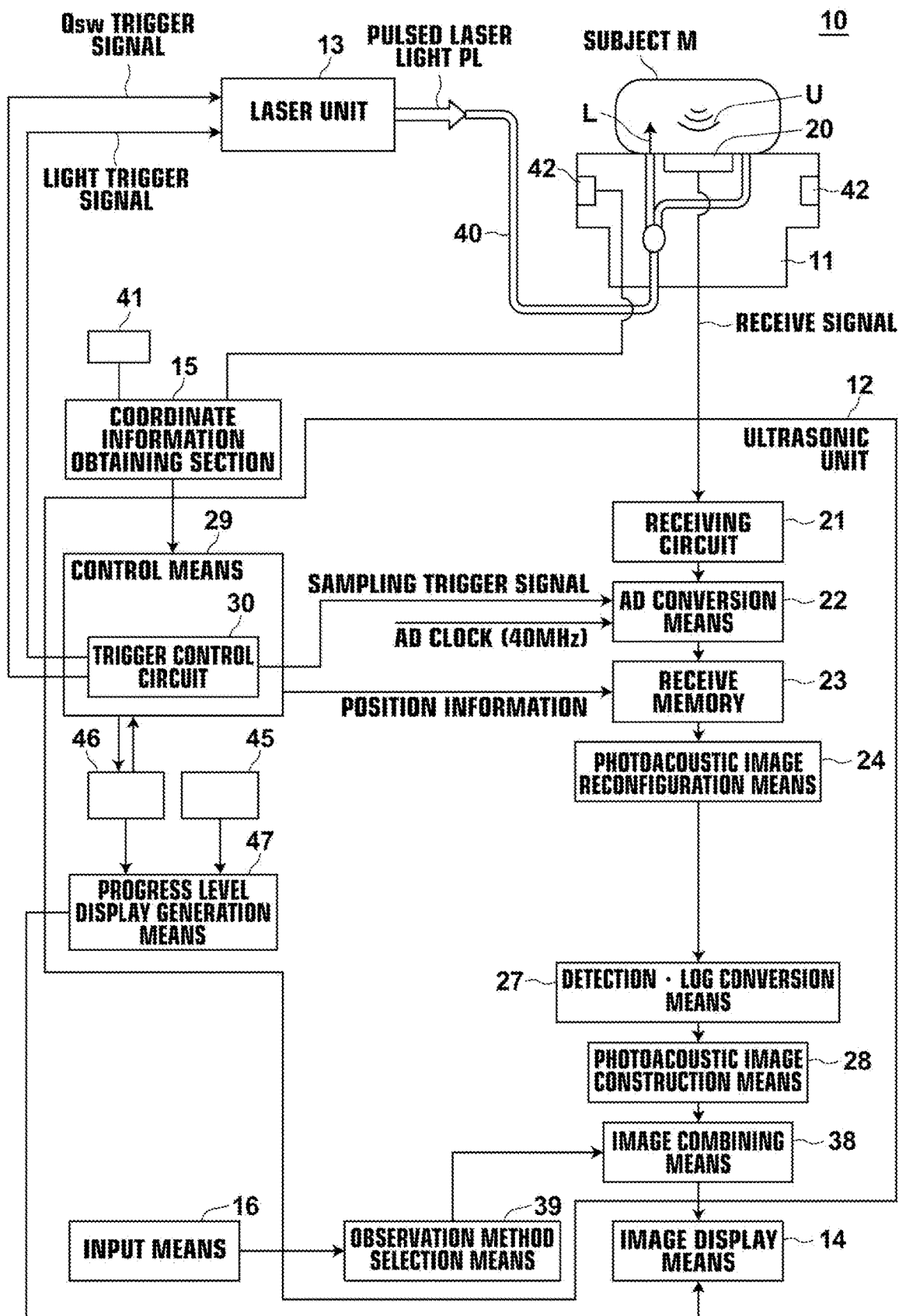
FIG. 1 is a schematic block diagram of an acoustic image generation apparatus (photoacoustic image generation apparatus) according to a first embodiment, illustrating the configuration thereof.

Hereinafter, embodiments of the present invention will be described, with reference to the accompanying drawings, but it should be appreciated that the present invention is not limited to these. Note that each component in the drawings is not necessarily drawn to scale in order to facilitate visual recognition.

Figure 2:
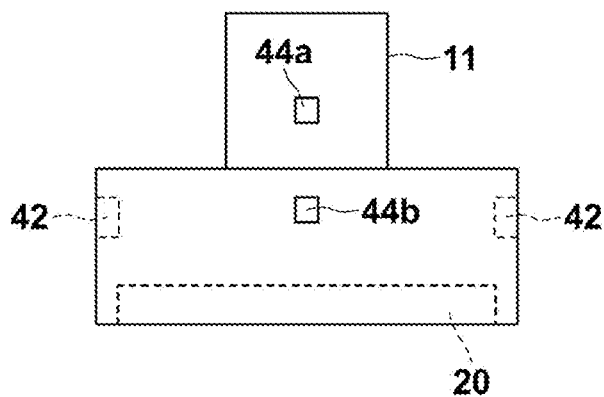
FIG. 2 is a schematic external view of the probe.
Figure 3:
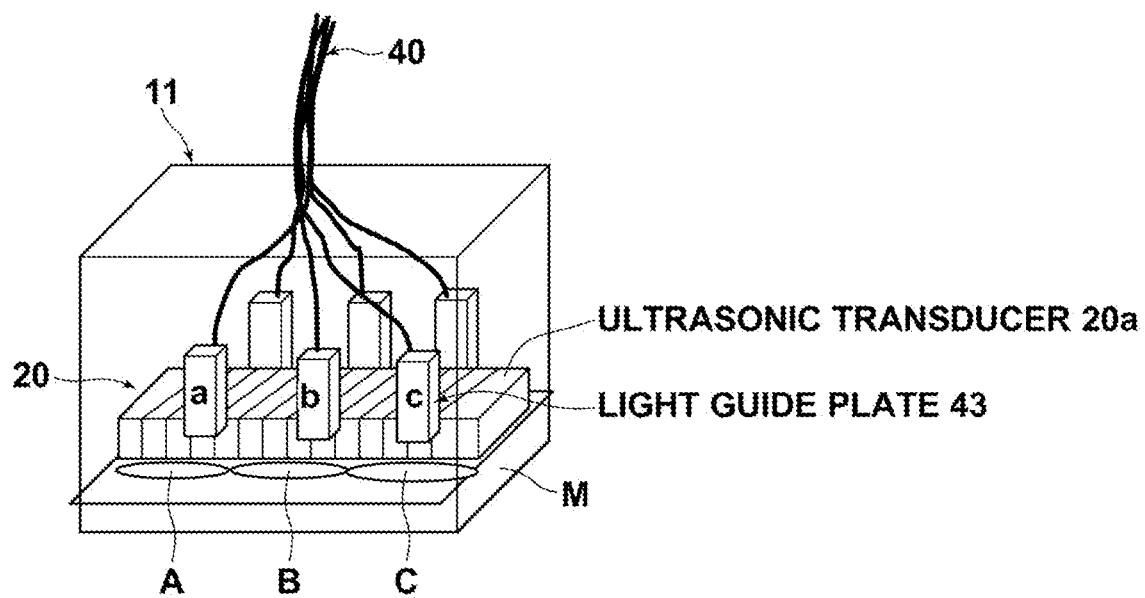
FIG. 3 is a schematic internal view of the probe.

First Embodiment of Acoustic Image Generation Apparatus and Progress Display Method A first embodiment of the present invention will be described first in detail. In the following description, a photoacoustic image generation apparatus will be taken up as a specific example of acoustic image generation apparatus. FIG. 1 is a block diagram of the photoacoustic image generation apparatus of the present embodiment, illustrating the configuration thereof. FIG. 2 is a schematic external view of the probe and FIG. 3 is a schematic interval view of the probe.

The photoacoustic image generation apparatus 10 of the present embodiment includes an ultrasonic probe (probe) 11, an ultrasonic unit 12, a laser unit 13, an image display means 14, coordinate obtaining means 15, 41, and 42, and an input means 16.

<Laser Unit>

The laser unit 13 outputs, for example, pulsed laser light PL as measuring light to be projected onto a subject M. The laser unit 13 is configured to output the pulsed laser light PL, for example, by receiving a trigger signal from a control means 29. The pulsed laser light PL outputted from the laser unit 13 is guided to the probe 11 using a light guide means, such as optical fiber, and projected onto the subject M from the probe 11.

Preferably, the laser unit 13 outputs pulsed light with a pulse width of 1 to 100 nsec as the pulsed laser light. For example, the laser unit 13 is a Q-switch (Qsw) laser in the present embodiment. In this case, the pulse width of the pulsed laser light PL is controlled, for example, by Qsw. The wavelength of the pulsed laser light is determined appropriately based on the light absorption characteristics of the measurement target substance within the subject. Hemoglobin in a living body generally absorbs light having a wavelength of 360 nm to 1000 nm, although having different light absorption characteristics depending on its state (oxygenated hemoglobin, deoxyhemoglobin, methemoglobin, or the like). Thus, if the measurement target is hemoglobin in a living body, the wavelength is preferably about 600 to 1000 nm which is relatively less absorbed by other living substances. Further, the wavelength of the laser light is preferably 700 to 1000 nm from the viewpoint that such light can reach a deep portion of the subject.

As for the laser unit 13, light emitting devices, such as semiconductor lasers (LDs), solid-state lasers, gas-lasers, and the like that generate a specific wavelength component or monochromatic light that includes the specific wavelength component may also be used.

<Probe (Ultrasonic Probe)>

The probe 11 detects, after the pulsed laser light PL outputted from the laser unit 13 is projected onto the subject M, a photoacoustic wave U (a photoacoustic signal) generated by a light absorbing body in the subject M by absorbing the pulsed laser light PL. The probe 11 has a transducer array 20 that includes a plurality of ultrasonic transducers 20a (acoustic detection elements) arranged, for example, one-dimensionally or two-dimensionally. The probe 11 is a handheld probe and is structured to allow the user to scan manually. Note that the scanning is not limited to be performed manually and may be performed by a mechanical mechanism.

The probe 11 includes two switches 44a and 44b exposed to outside, as illustrated, for example, in FIG. 2. The switch 44a is used when setting a target scanning length while the switch 44b is used at the start of scanning. The specific usage of the switches 44a and 44b will be described later. Note that the two switches are not necessarily essential elements in the present invention.

As illustrated, for example, in FIG. 3, the probe 11 is constituted by an optical fiber 40, a light guide plate 43, and the transducer array 20, and detects photoacoustic wave U from the subject M. The probe 11 is selected from the sector scanning type, linear scanning type, convex scanning type, and the like, as appropriate, according to the diagnostic target of subject M. In the present embodiment, a magnetic sensor 42 constituting a part of the coordinate obtaining means is built in the probe 11.

The optical fiber 40 and the light guide plate 43 are optical elements of a light projection means that projects the pulsed laser light PL onto the subject M from near the transducer array 20. As illustrated, for example, in FIG. 3, the light guide plate 43 is connected to a distal end portion of the optical fiber 40 that guides the pulsed laser light PL outputted from the laser unit 13 near the transducer array 20. The light guide plate 43 is disposed, for example, along the perimeter of the transducer array 20. A configuration may also be adopted wherein the pulse laser light PL outputted from the distal end portion of the optical fiber 40 is directly projected onto the subject M. Otherwise, in place of the light guide plate 43, the other optical element may be provided on the distal end portion of the optical fiber 40.

The transducer array 20 is a detection element that detects the photoacoustic wave U generated in the subject M. As illustrated, for example, in FIG. 3, the transducer array 20 is constituted by a plurality of ultrasonic transducers 20*a* disposed one-dimensionally. The ultrasonic transducer 20*a* is a piezoelectric element formed, for example, of piezoelectric ceramics or a polymer film, such as a polyvinylidene fluoride (PVDF) film or the like. When a photoacoustic wave U is detected, the ultrasonic transducer 20*a* has a function to convert a photoacoustic signal of the photoacoustic wave U to an electrical signal. The electrical signal is outputted to a receiving circuit 21 to be described later.

The projection of the pulsed laser light PL may be performed, for example, with respect to each partial region of the subject M. In such a case, a plurality of light guide plates 43 are provided corresponding to, for example, each of region A, region B, and region C (FIG. 3). In this case, if the region A is selected, the pulsed laser light PL is guided to a light guide plate 43*a* corresponding to the region A and projected onto the region A. If the region B is selected, the pulsed laser light PL is guided to a light guide plate 43*b* corresponding to the region B and projected onto the region B. Further, if the region C is selected, the pulsed laser light PL is guided to a light guide plate 43*c* corresponding to the region C and projected onto the region C. Alternatively, the projection of the pulsed laser light PL may be performed, for example, from all, of the light guide plates 43 in FIG. 3 at the same time.

<Coordinate Obtaining Means>

The coordinate obtaining means sequentially obtains a coordinate that defines the position and the posture of the probe 11 in real space (actual space) (hereinafter, also simply referred to as a coordinate) constantly or during the probe 11 is scanned. The term "obtains a coordinate" as used herein refers to obtaining information required for identifying the coordinate.

For example, in the present embodiment, the coordinate obtaining means is a magnetic sensor unit. The magnetic sensor unit is constituted by a coordinate information obtaining section 15, a magnetic field generation section 41, such as a transmitter and the like, and the magnetic sensor 42. The magnetic sensor unit may obtain a position (x, y, z) and a posture (angle) ($\alpha$, $\beta$, $\gamma$) of the magnetic sensor relative to a magnetic field generation section system space (space of the pulsed magnetic field formed by the magnetic field generation section). Then, the position and the posture of the magnetic sensor are related to the position and posture of the probe. The term "position of the magnetic sensor" as used herein refers to the position of the reference point of the magnetic sensor determined based on the coordinate obtained by the magnetic sensor. For example, if only one the magnetic sensor is provided, the reference point may be the coordinate itself obtained by the magnetic sensor, while if more than one magnetic sensor is provided, the reference point may be a new coordinate calculated based on the coordinates obtained by these magnetic sensors (center point of these coordinates or the like). The term "posture of the magnetic sensor" as used herein refers to, for example, the inclination of the space with the origin at the reference point of the magnetic sensor (magnetic sensor system space). If the scanning of the probe 11 is only translation, the information to be obtained may be only the relative position between the scanning start point and the current position of the probe.

In the present embodiment, the coordinate information obtaining section 15 calculates a coordinate from a value measured by the magnetic sensor unit and sends information of the coordinate to the ultrasonic unit 12. If an operation to reset to the origin is performed prior to the scanning of the probe 11, the coordinate information obtaining section 15 sets the position and the posture of the probe 11 at that time to the origin of the magnetic field generation section system space. This space is a three-axis space of (x, y, z) if considered, for example, only translation and a six-axis space of (x, y, z, $\alpha$, $\beta$, $\gamma$) if considered also rotational movement. It is preferable that the origin is set such that an axis of the space is aligned along an array direction (direction in which ultrasonic transducers 20*a* are disposed) or an elevation direction (direction perpendicular to the array direction and parallel to the detection surface of the transducer array 20) of the transducer array 20. The coordinate obtaining means may be configured to obtain the coordinate using an acceleration sensor, an infrared sensor, or the like, other than the magnetic sensor unit.

For example, the coordinate obtaining means constantly obtains the coordinate of the probe 11, for example, at a predetermined period (coordinate obtaining period). A shorter coordinate obtaining period allows more accurate position of the probe 11 to be obtained. The obtained coordinate is sent to the control means 29. This coordinate is used when generating three-dimensional volume data based on acoustic signals, generating tomographic data from the volume data, or arranging two-dimensional acoustic images in order according to the position. In the present invention, progress of scanning process is displayed based on the coordinate. Preferably, the coordinate obtaining period is synchronized with the output period of pulsed laser light and the construction period of one-frame photoacoustic image. Otherwise, it may be a period obtained by skipping ⅓ from the output period of pulsed laser light and the construction period of one-frame photoacoustic image in order to reduce the calculation load.

<Ultrasonic Unit>

The ultrasonic unit 12 includes a receiving circuit 21, an AD conversion means 22, a receive memory 23, a photoacoustic image reconfiguration means 24, a detection•log conversion means 27, a photoacoustic image construction means 28, the control means 29, an image combining means 38, an observation method selection means 39, a scanning length setting means 45, a scanned length calculation means 46, and a progress level display generation means 47. The receiving circuit 21, AD conversion means 22, receive memory 23, photoacoustic image reconfiguration means 24, detection•log conversion means 27, and photoacoustic image construction means 28 correspond, as a unit, to the acoustic image generation means of the present invention.

The control means 29 controls each section of the photoacoustic image generation apparatus 10 and includes a trigger control circuit 30 in the present embodiment. The trigger control circuit 30 sends a light trigger signal to the laser unit 13 when, for example, activating the photoacoustic image generation apparatus. This causes a flash lamp in the laser unit 13 to be turned on and excitation of the laser rod is started. The excitation state of the laser rod is maintained and the laser unit 13 becomes ready to output pulsed laser light.

Then, the control means 29 sends a Qsw trigger signal to the laser unit 13 from the trigger control circuit 30. That is, the control means 29 controls the output timing of the pulsed laser light from the laser unit 13 by the Qsw trigger signal. Further, the control means 29 sends a sampling trigger signal to the AD conversion means 22 simultaneously with the transmission of the Qsw trigger signal in the present embodiment. The sampling trigger signal serves as a timing signal to start sampling of the photoacoustic signal in the AD conversion means 22. In this way, the use of the sampling trigger signal allows the photoacoustic signal to be sampled in synchronization with the output of the pulsed laser light. For example, the control means 29 may be configured to start transmission of the Qsw signal when the switch 44b of the probe 11 is pressed. Such configuration allows the position of the probe 11 at the time when the switch 44b is pressed to be treated as the scanning start point.

Further, in the present embodiment, the control means 29 is configured to terminate the photoacoustic image generation process (e.g., to stop the output of pulsed laser light or the like) when a message indicating that the variation in the scanned length is greater than or equal to a predetermined value is received from the scanned length calculation means 46. Such configuration allows the generation process to be terminated promptly if an erroneous operation occurs, such as dropping of the probe 11 or the like. In this case, only a portion of the photoacoustic image generated properly may be displayed.

The receiving circuit 21 receives a photoacoustic signal detected by the probe 11. The photoacoustic signal received by the receiving circuit 21 is sent to the AD conversion means 22.

The AD conversion means 22 is a sampling means, and samples the photoacoustic signal received by the receiving circuit 21 and converts it to a digital signal. For example, the AD conversion means 22 includes a sampling control section and AD converter. The receive signal received by the receiving circuit 21 is converted to a digitized sampled signal by the AD converter. The AD converter is controlled by the sampling control section and configured to perform sampling when a sampling trigger signal is received by the sampling control section. The AD conversion means 22 samples the receive signal at a predetermined sampling period based on, for example, an AD clock signal of predetermined frequency inputted from outside.

The receive memory 23 stores the photoacoustic signal sampled by the AD conversion means 22 (i.e., the sampled signal described above). In the present invention, the receive memory 23 also stores the coordinate of the probe 11 in the magnetic field generation section system obtained by the coordinate information obtaining section 15. Then, the receive memory 23 outputs the photoacoustic signal detected by the probe 11 to the photoacoustic image reconfiguration means 24.

The photoacoustic image reconfiguration means 24 reads the photoacoustic signal from the receive memory 23 and generates data of each line of a photoacoustic image based on the photoacoustic signal detected by the transducer array 20 of the probe 11. The photoacoustic image reconfiguration means 24 generates data of one line by adding up, for example, data from 64 ultrasonic transducers of the probe 11 at delay times corresponding to the positions of the ultrasonic transducers (delay-and-sum method). The photoacoustic image reconfiguration means 24 may perform the reconfiguration by the CBP (Circular Back Projection) method in place of the delay-and-sum method. Otherwise, the photoacoustic image reconfiguration means 24 may perform the reconfiguration by the Hough transform method or the Fourier transform method.

The detection·log conversion means 27 obtains an envelope of the data of each line and performs log conversion on the obtained envelope.

The photoacoustic image construction means 28 constructs a photoacoustic image of one frame based on the log-converted data of each line. The photoacoustic image construction means 28 constructs a photoacoustic image, for example, by converting the position of the potoacoustic signal (peak portion) in the time axis direction to the position in the depth direction of the photoacoustic image.

The observation method selection means 39 selects a display mode of the photoacoustic image. As for the display mode of the volume data of photoacoustic signal, for example, a three-dimensional image display mode, a tomographic image display mode, and a graphic display mode on a predetermined axis may be cited. Which display mode is to be used for the display is determined by initial setting or selected according to the user input via the input means 16.

The image combining means 38 generates volume data using the sequentially obtained coordinate of the probe 11 and the photoacoustic signal obtained at each coordinate. The generation of the volume data is performed by allocating the signal value of each photoacoustic signal in a virtual space according to the coordinates related to each photoacoustic image frame and pixel coordinates in the photoacoustic image. For example, the coordinate when the Qsw trigger signal is sent, the coordinate when the light is actually outputted, the coordinate when the sampling of the photoacoustic signal is started, and the like are related to each photoacoustic image frame. In allocating signal values, if positions where signal values are to be allocated overlap, for example, an average value or a maximum value of the signals is used as the signal value of the overlapped positions. Further, if no signal value to be allocated is present, an interpolation is preferably performed, as required, using signal values of adjacent positions. For example, the interpolation is performed by allocating a weighted average of four proximal points in order from the most proximal point to the interpolating position. This allows more natural form of volume data to be generated. The image combining means 38 further performs necessary processing (e.g., scale correction, coloring according to the voxel value, and the like) on the generated volume data.

Figure 4A:
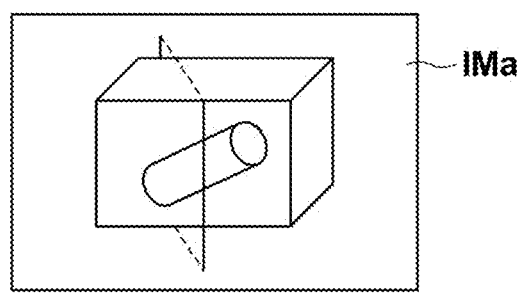
FIG. 4A is a schematic view, illustrating an example display mode of an acoustic image (photoacoustic image).
Figure 4B:
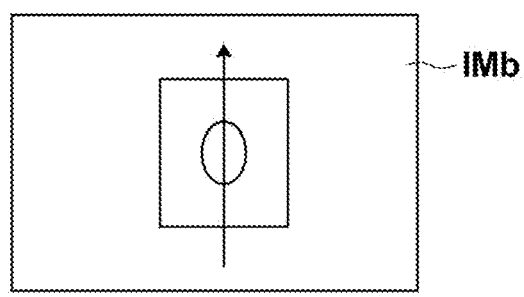
FIG. 4B is a schematic view, illustrating an example display mode of an acoustic image (photoacoustic image).
Figure 4C:
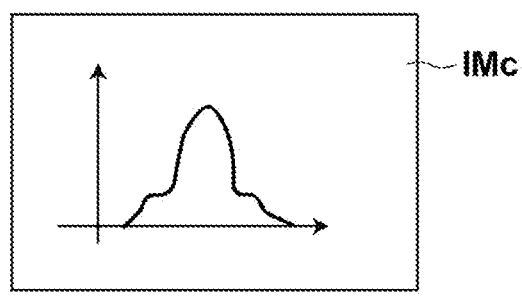
FIG. 4C is a schematic view, illustrating an example display mode of an acoustic image (photoacoustic image)

Further, the image combining means 38 generates a photoacoustic image according to the observation method selected by the observation method selection means 39. FIGS. 4A to 4C are schematic views, illustrating example display modes. FIG. 4A is a three-dimensional image IMa representing values of volume data viewed from a predetermined viewpoint in the virtual space. If an observation method for observing a three-dimensional absorption distribution is selected at the observation method selection means 39, the three-dimensional image IMa shown in FIG. 4A is displayed. The viewpoint that defines the three-dimensional image IMa in the virtual space is already set in the observation method selection means 39, for example, by initial setting or through the user input via the input means 16, and this information is also sent to the image combining means 38. FIG. 4B is a cross-sectional image IMb representing values on a cross-section by a predetermined two-dimensional plane. If an observation method for observing a two-dimensional absorption distribution is selected at the observation method selection means 39, the cross-sectional image IMb shown in FIG. 4B is displayed. The two-dimensional plane that defines the cross-sectional image IMb is already set in the observation method selection means 39, for example, by initial setting or through the user input via the input means 16, and this information is also sent to the image combining means 38. FIG. 4C is a graph IMc representing values of volume data along a predetermined one-dimensional axis. If an observation, method for observing a one-dimensional absorption distribution is selected at the observation method selection means 39, the graph IMc shown in FIG. 4C is displayed. The one-dimensional axis that defines the graph IMc is already set in the observation method selection means 39, for example, by initial, setting or through the user input via the input means 16, and this information is also sent to the image combining means 38.

The photoacoustic image generated according to the selected observation method is the final image to be displayed on the image display means 14 (display image). In the photoacoustic image generation method described above, it should be appreciated that, after a photoacoustic image is generated, the user may rotate or move the image, as required. That is, in the case where a three-dimensional image identical to that shown in FIG. 4A is displayed, if the user sequentially specifies or moves the direction of viewpoint using the input means 16, the photoacoustic image will be recalculated and the three-dimensional image will be rotated. The user may also change the observation method, as appropriate, using the input means 16.

The scanning length setting means 45, the scanned length calculation means 46, and the progress level display generation means 47 perform the function of generating the progress level display that indicates progress in scanning process of the probe for generation a photoacoustic image described above. The "progress level display" as used herein refers to a letter display, a graphic display, a symbol display, and other similar displays that facilitate visual recognition of the progress level of the scanning process.

Figure 5:
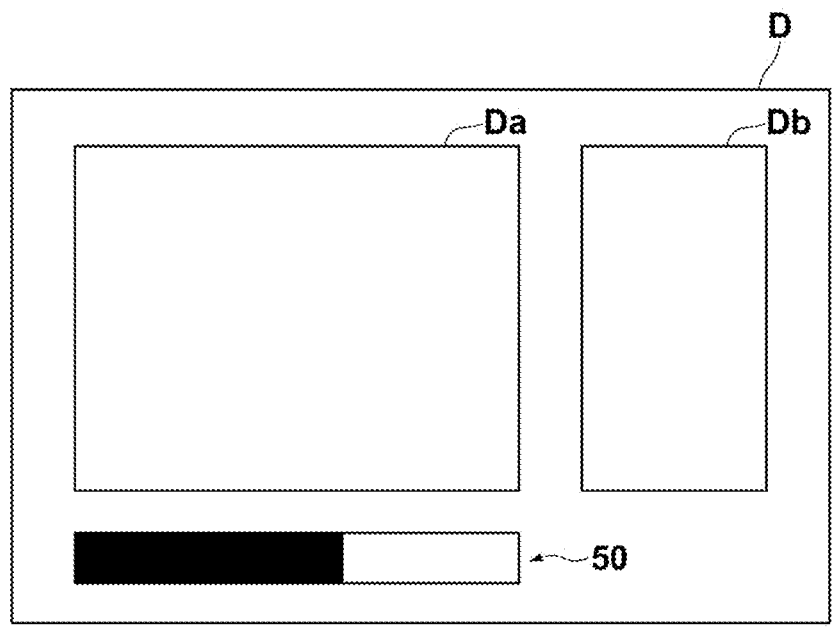
FIG. 5 is a schematic view of an example screen configuration displayed on an image display means.
Figure 6A:
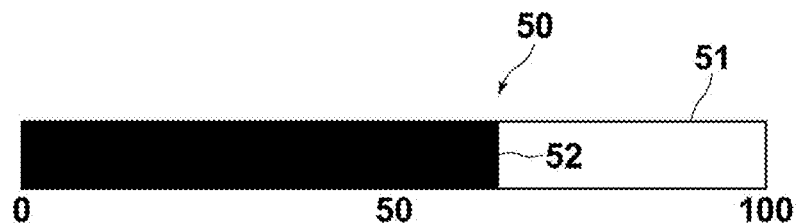
FIG. 6A is a schematic view, illustrating an example progress meter configuration.
Figure 6B:
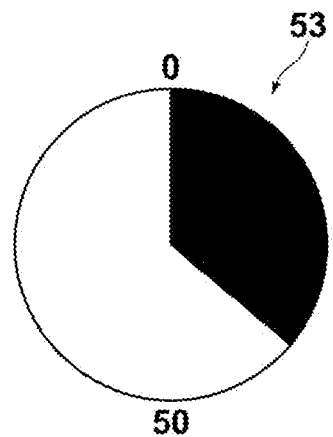
FIG. 6B is a schematic view, illustrating an example progress meter configuration.

FIG. 5 is a schematic view of an example screen configuration displayed on the image display means. FIGS. 6A and 6B are schematic views, illustrating example configurations of the progress level display.

The progress level display of the present invention is displayed on the screen with the photoacoustic image at the same time (FIG. 5) to allow the user to easily confirm the progress. FIG. 5 shows an area Da in which a photoacoustic image is displayed, an area Db in which character information, such as the patient information (identifying ID, age, weight, and the like) and imaging conditions (imaging region, target scanning length, and the like) is displayed, and a progress bar 50 displayed on the screen D of the image display means 14 at the same time. In the present embodiment, the progress bar 50 is the progress level display in the present invention.

As illustrated in FIG. 6A, the progress bar 50 is a bar graph like progress meter, and is primarily composed of a gauge 51 which is the outer frame and an indicator 52 representing the progress level of scanning process. Further, a progress level scale is provided near the bottom of the gauge 51 but it is not necessarily essential. In the progress bar 50 shown in FIG. 6A, the indicator 52 increases or decreases according to the progress level and the progress level is indicated at the position of the right edge of the indicator 52.

For the progress level display, for example, a circular graph progress meter 53 shown in FIG. 6B may also be used other than the progress bar 50 described above. In the progress meter 53, for example, the progress level is indicated by a sector-shaped indicator by increasing or decreasing the center angle (i.e., area of the sector) (FIG. 6B). Note that, in the case of a circular graph progress meter, a configuration may be adopted wherein the progress level is indicated by increasing or decreasing the radius of the circular indicator area of the circle) according to the progress level. The progress level display may be a direct indication of the numerical value of progress level on the screen other than the aforementioned graphic progress meters.

Figure 8:
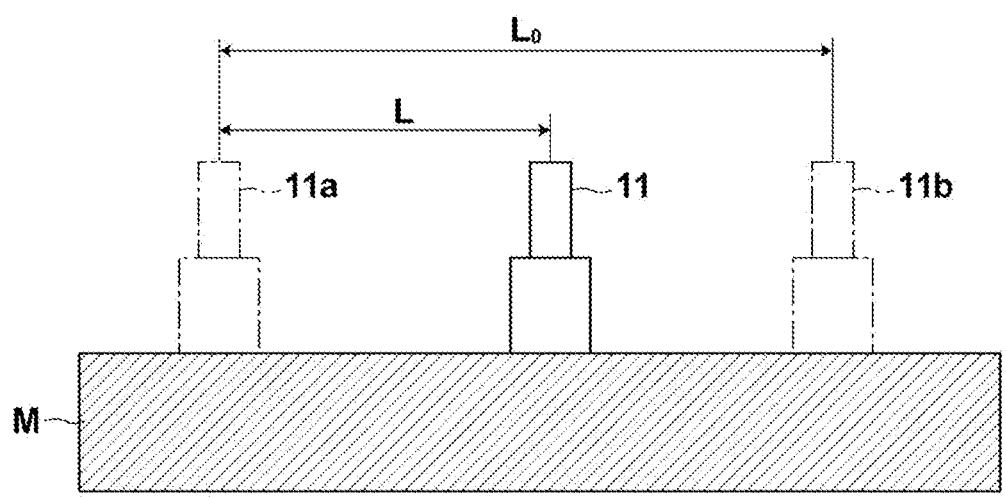
FIG. 8 is a schematic view illustrating the relationship between scanned length and target scanning length.

FIG. 7 is a flowchart illustrating scanning process steps of the probe. FIG. 8 a schematic view illustrating the relationship between scanned length and target scanning length.

The scanning length setting means 45 sets a target length of scanning the probe 11 (target scanning length). The target scanning length is set prior to the scanning process of the probe 11 (FIG. 7). The target scanning length is set, for example, by setting a numerical value arbitrarily inputted by the user. The target scanning length may also be set by setting a numerical value selected from predetermined 3 to 5 candidates (e.g., 10 mm, 30 mm, 50 mm, 70 mm, and 90 mm, and the like). If such is the case, time and effort of the user to input, point by point, the numerical value prior to the scanning process may be saved. Further, the target scanning length may be set by specifying a range to be actually scanned using the switch 44a for setting scanning length. More specifically, as illustrated in FIG. 8, the probe 11 is placed at the scanning start point as illustrated by the symbol 11a and the switch 44a is pressed to obtain the coordinate of the scanning start point. Then, the probe 11 is placed at the scanning end point as illustrated by the symbol 11b and the switch 44a is pressed to obtain the coordinate of the scanning end point. The length of the distance between these coordinates is set as the target scanning length. If such is the case, the target scanning length may be set intuitively without considering a specific numerical value of the length of the range to be actually scanned by the probe 11. The operation using the switch 44a described above is the operation to simply obtain the length, and the route connecting between the scanning start point and the scanning end point is not necessarily corresponds to the route to be actually scanned.

The scanned length calculation means 46 calculates the scanned length (distance from the scanning start point to the current position of the probe 11) after the scanning of the probe 11 is started. The scanned length is calculated based on the coordinate of the probe 11 sequentially obtained by the coordinate obtaining means. In the present invention, the distance between the positions of the magnetic sensor before and after the scanning may be used as the scanned length.

Figure 9A:
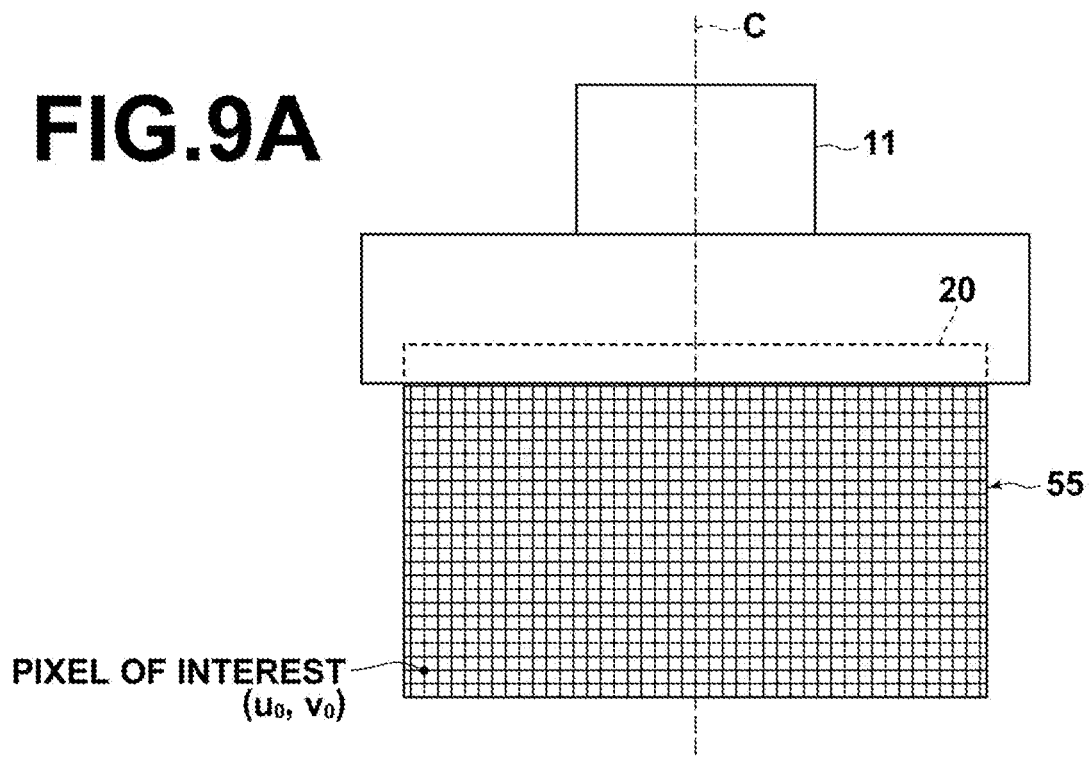
FIG. 9A is a schematic front view, illustrating the positional relationship between an imaging area, the center axis of the probe, and a pixel of interest.
Figure 9B:
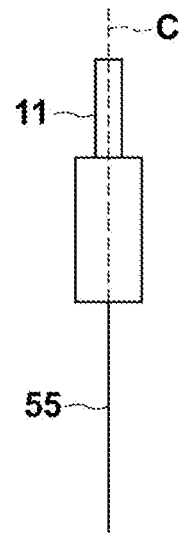
FIG. 9B is a schematic side view, illustrating the positional relationship between the imaging area, the center axis of the probe, and the pixel of interest.
Figure 10:
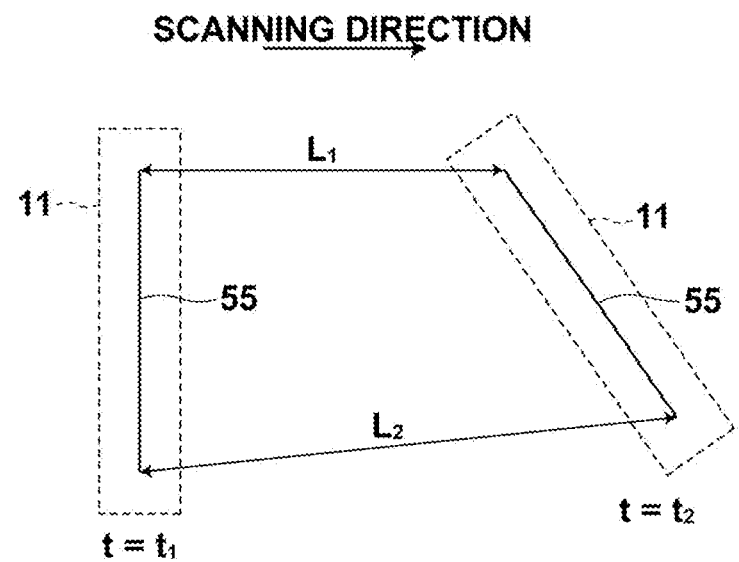
FIG. 10 is a schematic view, illustrating the relationship between the posture of the probe and travel distance of pixels in the imaging area.

But, it is preferable that the scanned length is calculated by calculating a coordinate of a pixel (pixel of interest in FIG. 9A) included in the imaging area 55 defined by the probe 11 and located remote from the center axis of the probe in the real space based on the coordinates of the probe 11 in the real space, and based on the coordinate of the pixel in the real space, for the following reasons. As an example, FIG. 10 illustrates the state in which the posture of the probe 11 at the scanning endpoint (t=t2) is rotated centered on the center axis C of the probe 11 (e.g., axis passing through the center of the transducer array 20 and perpendicular to the detection surface thereof) with respect to the posture of the probe 11 at the scanning start point (t=t1). Further, FIG. 10 is a drawing of the probe 11 shown in FIG. 93 viewed from above. Now, considering the case in which the reference point of the magnetic sensor is on the center axis C. In such a case, the length between pixels before and after the scanning may sometimes differ from the length between the positions of the magnetic sensor before and after the scanning due to the rotation at a position remote from the center axis C of the probe 11. More specifically, the scanned length $L_1$ of a pixel which came closer to the scanning start point due to the rotation becomes shorter than the length between the positions of the magnetic sensor before and after the scanning while the scanned length $L_2$ of a pixel which came away from the scanning start point due to the rotation becomes longer than the length between the positions of the magnetic sensor before and after the scanning. Here, considering that the target scanning length is set such that the length of the three-dimensional acoustic image to be finally obtained becomes a desired length, it can be said that, in actuality, it is necessary to accurately calculate the length between pixels before and after the scanning. Therefore, it is concluded as above.

More specifically, the variation in the position of a pixel of interest in the imaging area 55 in the magnetic field generation section system space (real space) is set as the scanned length L. In this case, the scanned length L is calculated by Formula 1 given below.

$$L = \sqrt{(X-X_0)^2 + (Y-Y_0)^2 + (Z-Z_0)^2} \qquad \text{Formula 1}$$

In Formula 1, $(X_0, Y_0, Z_0)$ is the position of the pixel of interest at the scanning start point in the magnetic field generation section system space and $(X, Y, Z)$ is the position of the pixel of interest at the current position of the probe 11 in the magnetic field generation section system space. Here, if the relative relationship of the magnetic sensor system space to the magnetic field generation section system space is $(x, y, z, \alpha, \beta, \gamma)$, the $(X, Y, Z)$ of the pixel of interest with the coordinate $(u_0, v_0)$ in the imaging area system space may be obtained by a conversion equation represented by Formula 2 given below.

$$\begin{bmatrix} X \\ Z \\ Y \\ 1 \end{bmatrix} = \begin{bmatrix} \text{rot\_SM} & \text{para\_SM} \\ 0\ 0\ 0 & 1 \end{bmatrix} \begin{bmatrix} \text{rot\_PS} & \text{para\_PS} \\ 0\ 0\ 0 & 1 \end{bmatrix} \begin{bmatrix} u_0 \\ 1 \\ v_0 \\ 1 \end{bmatrix} \qquad \text{Formula 2}$$

in Formula 2, the first term on the right side represents the coordinate transformation term from the magnetic sensor system space S to the magnetic field generation section system space M, and the second term on the right side represents the coordinate transformation term from the imaging area system space P to the magnetic sensor system space S. The rot_SM and rot_PS represent angular components of the respective coordinate transformation terms, while para_SM and para_PS represent displacement components of the respective coordinate transformation terms. The rot_SM, para_SM, rot_PS, and para_PS may be represented by Formulae 3 to 6 respectively.

$$\text{rot\_SM} = \begin{pmatrix} \cos\alpha & -\sin\alpha & 0 \\ \sin\alpha & \cos\alpha & 0 \\ 0 & 0 & 1 \end{pmatrix} \begin{pmatrix} \cos\beta & 0 & \sin\beta \\ 0 & 1 & 0 \\ -\sin\beta & 0 & \cos\beta \end{pmatrix} \begin{pmatrix} 1 & 0 & 0 \\ 0 & \cos\gamma & -\sin\gamma \\ 0 & \sin\gamma & \cos\gamma \end{pmatrix} \qquad \text{Formula 3}$$

$$\text{para\_SM} = (x, y, z) \qquad \text{Formula 4}$$

$$\text{rot\_PS} = \begin{pmatrix} \cos\alpha_1 & -\sin\alpha_1 & 0 \\ \sin\alpha_1 & \cos\alpha_1 & 0 \\ 0 & 0 & 1 \end{pmatrix} \qquad \text{Formula 5}$$

$$\begin{pmatrix} \cos\beta_1 & 0 & \sin\beta_1 \\ 0 & 1 & 0 \\ -\sin\beta_1 & 0 & \cos\beta_1 \end{pmatrix} \begin{pmatrix} 1 & 0 & 0 \\ 0 & \cos\gamma_1 & -\sin\gamma_1 \\ 0 & \sin\gamma_1 & \cos\gamma_1 \end{pmatrix}$$

$$\text{para\_PS} = (x_1, y_1, z_1) \qquad \text{Formula 6}$$

In Formulae 5 and 6, the $(x_1, y_1, z_1, \alpha_1, \beta_1, \gamma_1)$ represents the coordinate of the origin of the imaging area system space P in the magnetic sensor system space S. This coordinate is a known value determined by the design of the probe 11.

Preferably, if a scanned length is calculated, the scanned length calculation means 46 also calculates a variation in the scanned length by comparing the current scanned length with a scanned length calculated previously (e.g., immediately preceding the current scanned length). Then, if the variation is greater than or equal to a predetermined value (e.g., 10 cm), a message so indicating is sent to the control means 29. The variation in scanned length may be calculated, for example, by storing the immediately preceding coordinate $(X_1, Y_1, Z_1)$ of the probe 11 in a memory and obtaining, using the current coordinate $(X, Y, Z)$, the distance between these coordinates.

The progress level display generation means 47 receives the target scanning length from the scanning length setting means 45 and the scanned length from the scanned length calculation means 46, and calculates the progress level based on the target scanning length and the scanned length. In the present embodiment, the progress level display generation means 47 generates the progress bar 50 in which the indicator is varied according to the progress level. Information or data of the progress bar 50 are outputted to the image display means 14. The progress level may be expressed by Formula 7 given below using, for example, the target scanning length $L_0$ and current scanned length L in FIG. 8.

$$\text{PROGRESS LEVEL} = L/L_0 \qquad \text{Formula 7}$$

The image display means 14 displays the display image generated by the image combining means 38 and the progress level display generated by the progress level display generation means.

Hereinafter, steps in the scanning process of the probe 11 will be described with reference to FIG. 7.

First, in STEP 1, a target scanning length $L_0$ is set. The setting of the target scanning length is as described earlier. Next, in STEP 2, a scanning process of the probe 11 is started, and the coordinate obtaining means 15, 41, and 42 continue to obtain coordinates in succession at least until the end of the scanning process. The start of the scanning may be judged, for example, based on the time when the switch 44b of probe 11 is pressed, when the foot switch (not shown) is pressed, when a photoacoustic signal is first detected, or the like. Then, in STEP 3, only the gauge of the progress bar 50 is displayed. Note that the gauge display timing is not limited to the timing in the present embodiment.

Then, in STEP 4, the initial coordinate (initial sensor value) of the magnetic sensor $(x_0, y_0, z_0, \alpha_0, \beta_0, \gamma_0)$ is obtained. Next, in STEP 5, the initial coordinate $(X_0, Y_0, Z_0)$ of a pixel of interest with the coordinate $(u_0, v_0)$ in the imaging area system space is obtained from the initial sensor value using the conversion equation described above. Then, in STEP 6, the coordinate (sensor value) of the magnetic sensor $(x, y, z, \alpha, \beta, \gamma)$ after one period is obtained, and from the sensor value, the current coordinate $(X, Y, Z)$ of the pixel of interest with the coordinate $(u_0, v_0)$ in the imaging area system space is obtained using the conversion equation described above.

At this time, in STEP 7, a variation from the initial coordinate $(X_0, Y_0, Z_0)$ of the pixel of interest calculated immediately before (i.e., calculated initially, in this case) to the current coordinate $(X, Y, Z)$ and a determination is made whether or not the variation is greater than or equal to a predetermined value. If the variation is greater than or equal to the predetermined value (i.e., if the coordinate is outside an appropriate range), the scanning process is determined to be terminated, and the pulsed laser light and the obtaining of the coordinate are terminated, whereby the scanning process is finished. On the other hand, if the variation is less than the predetermined value (i.e., if the coordinate is in appropriate range), the scanning process is continued and proceeds to STEP 8.

In STEP 8, a scanned length L is calculated from the current coordinate (X, Y, Z) of the pixel of interest and the initial coordinate ($X_0$, $Y_0$, $Z_0$) of the pixel of interest at the scanning start point. Then, in STEP 9, the indicator 52 is increased or decreased according to the progress level and displayed on the screen. Next, in STEP 10, a determination is made as to whether or not the scanned length L has reached the target scanning length $L_0$. At this time, if the scanned length L has reached the target scanning length $L_0$, the scanning process is determined to have been completed. Otherwise, STEP 6 and onwards will be performed again. A configuration may be adopted wherein the coordinate obtaining operation is terminated at the same time with the termination of the scanning process or when the switch 44*b* or the footswitch is pressed again.

As described above, according to the acoustic image generation apparatus and the progress display method of the present embodiment, it is possible, in a scanning process in which a probe having an ultrasonic transducer is scanned in generating an acoustic image, to sequentially obtain a coordinate of the probe in real space, calculate a scanned length based on the sequentially obtained coordinate, and generate a progress level display that indicates progress of the scanning process based on the predetermined target scanning length and the scanned length. As a result, the user of the probe may visually confirm the progress, so that, in generating an acoustic image by scanning the probe, progress of the scanning process may be confirmed easily.

<Design Changes>

In the foregoing, the description has been made of a case in which the progress level display is a progress bar formed of only a gauge and an indicator, but the present invention is not limited to this.

For example, the progress meter preferably has a scanning assist display that assists the scanning of the probe 11 such that the scanning process is completed properly. The term "such that the scanning process is completed properly" as used herein refers to that the scanning process is completed such that an acoustic image of desired quality is obtained. Factors that degrade the quality of an acoustic image may include variations in the scanning speed of the probe 11, and the like.

Figure 11:
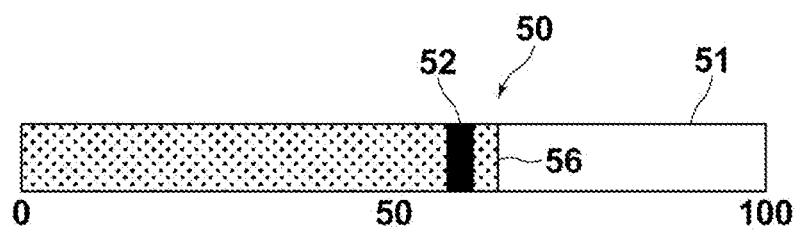
FIG. 11 is a schematic view, illustrating a configuration of the progress meter in the case in which the progress meter has a scanning assist display.
Figure 12A:
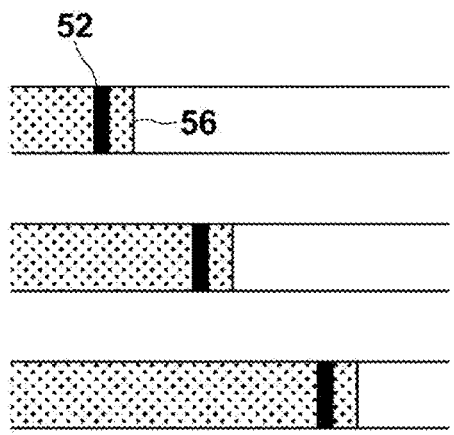
FIG. 12A is a schematic view, illustrating an example operation mode of an ideal velocity display and scanning restriction display.
Figure 12B:
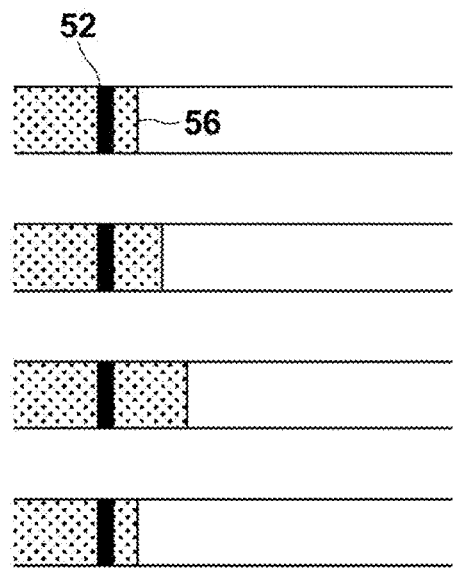
FIG. 12B is a schematic view, illustrating an example operation mode of an ideal velocity display and scanning restriction display.
Figure 12C:
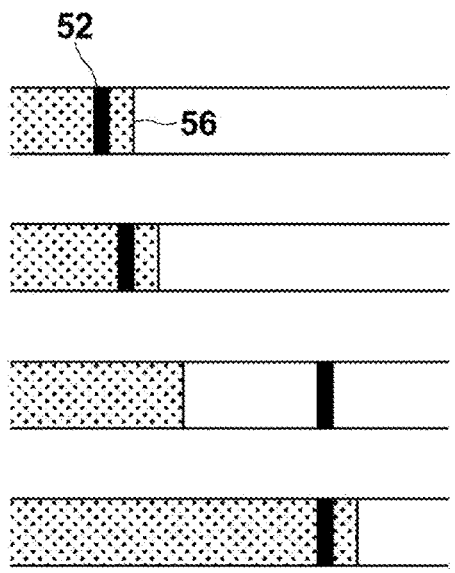
FIG. 12C is a schematic view, illustrating an example operation mode of an ideal velocity display and scanning restriction display.

Consequently, the present invention preferably includes an ideal speed display that guides the scanning of the probe 11 such that the scanning speed of the probe 11 becomes a predetermined value. For example, as illustrated in FIG. 11, a progress bar 50 having a gauge 51, a narrow indicator 52 with a constant width, and an ideal speed display 56 that will guide the scanning may be employed as the progress level display. As illustrated, for example, in FIG. 12A, the ideal speed display 56 may be a constant speed index that moves at a constant ideal speed in the forward direction of the progress bar 50 (higher progress level direction) adjacent to the indicator 52. The term "ideal speed" as used herein is a speed determined from the viewpoint of preventing missing in an acoustic image due to excessively fast scanning of the probe 11 and a specific value is determined appropriately according to acoustic image generation conditions. This allows the user to approximate the scanning speed of the probe 11 to the ideal speed by scanning the probe 11 such that the indicator 52 follows the ideal speed display 56. As a result, missing in an acoustic image is inhibited and a more accurate acoustic image may be obtained. The ideal speed display 56 advances, in principle, independently of the indicator 52. But, a configuration may be adopted in which, when the distance between a position indicated by the constant speed index and a position indicated by the indicator 52 becomes greater than or equal to a predetermined value, as illustrated in FIGS. 12B and 12C, the movement is resumed from the position indicated by the indicator 52. When the distance between the position indicated by the indicator 52 and the position indicated by the ideal speed display becomes large, this allows the user to reduce the distance to make it easy to follow the ideal speed display 56. The aforementioned predetermined value may be set as appropriate.

Note that the ideal speed display is not limited to the constant speed index described above and it may be a speed meter that indicates the relationship between the current scanning speed and the ideal scanning speed.

Figure 12D:
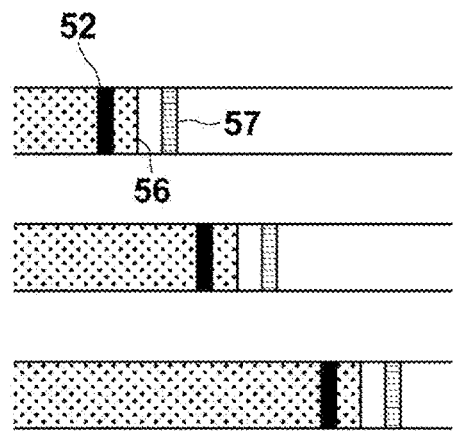
FIG. 12D is a schematic view, illustrating an example operation mode of an ideal velocity display and scanning restriction display.

Further, the progress meter may include a scanning limit display 57 that guides the scanning of the probe such that the scanning speed of the probe falls within a predetermined range. The term "to guide the scanning of the probe such that the scanning speed of the probe falls within a predetermined range" is, in other words, to indicate an appropriate range (or allowable range) of difference between the actual and ideal scanning speeds of the probe (i.e., deviation from the ideal scanning speed). The scanning limit display 57 may be, as illustrated, for example, in FIG. 12D, an upper limit index that indicates a position corresponding to an upper limit value in variation of the coordinate (position) of the probe 11 in relation to the position indicated by the indicator 52. This allows the upper limit of variation of the probe 11 when the coordinate is obtained next time to be visually indicated. As a result, missing in an acoustic image is inhibited and a more accurate acoustic image may be obtained. The position indicated by the scanning limit display 57 may be set arbitrarily and, for example, it may be a position at a predetermined distance (e.g., 5% of the width of the gauge) with reference to the position indicated by the indicator 52 or the position indicated by the ideal speed display described above. If the indicator 52 is scanned over the scanning limit display 57, an alert is issued, for example, changing the color of the indicator 52 or giving a sound for calling attention. Further, for example, only a portion of the photoacoustic image generated properly may be displayed.

Figure 13:
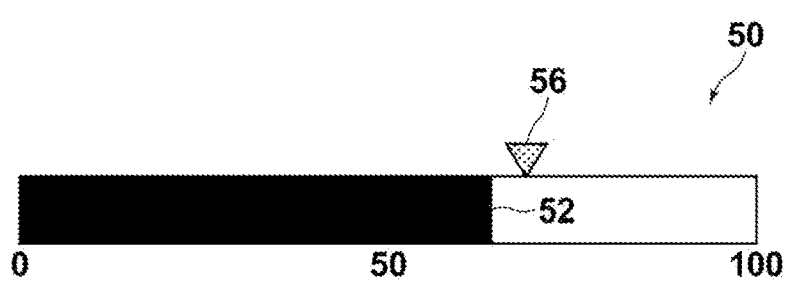
FIG. 13 is a schematic view, illustrating another form of ideal velocity display.

The ideal speed display 56 is not limited to be disposed inside the gauge of the progress meter as long as the function thereof is secured. For example, the ideal speed display 56 may be an index disposed outside the gauge, as illustrated in FIG. 13. Likewise, the scanning limit display 57 may also be an index disposed outside the gauge.

Figure 14:
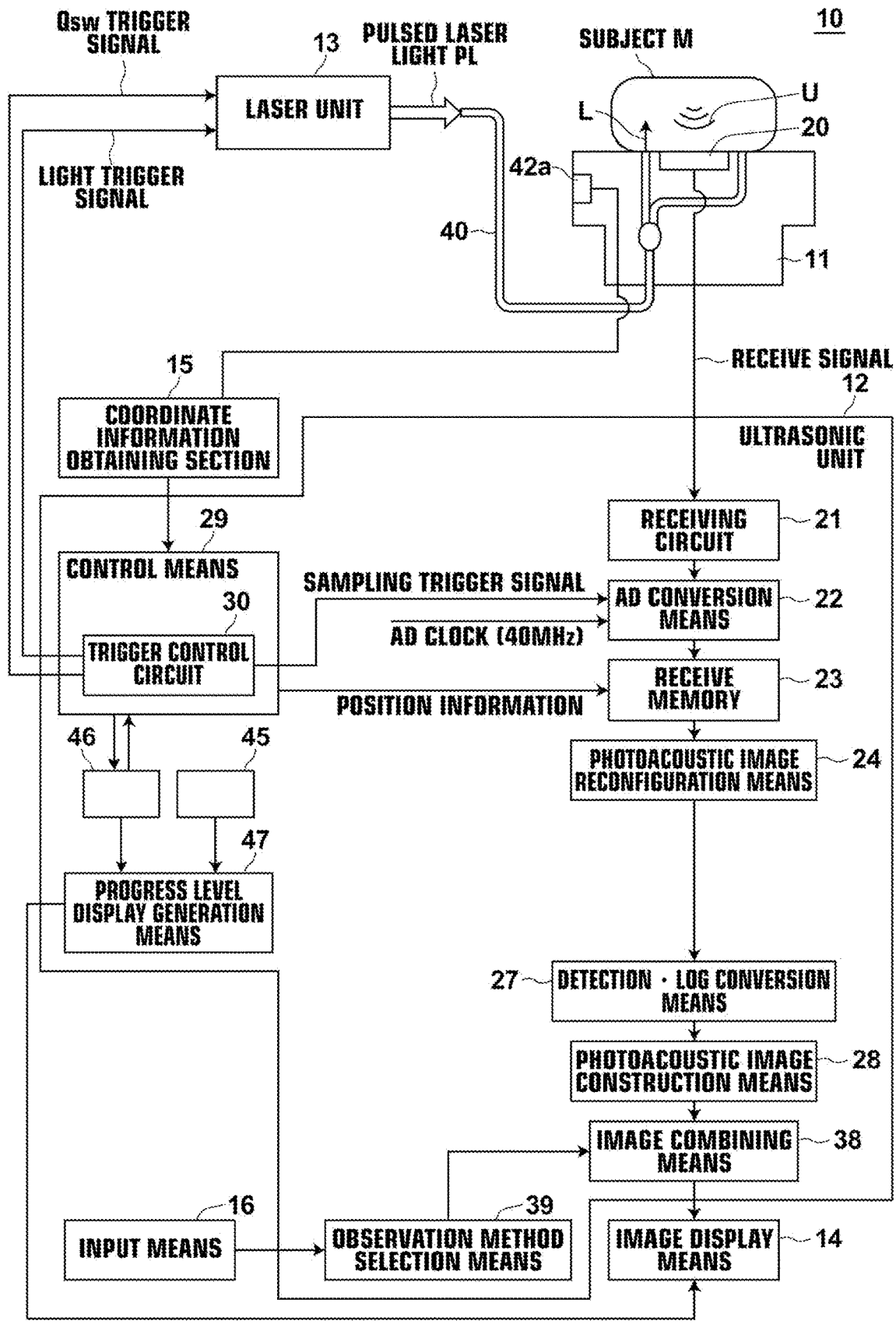
FIG. 14 is a schematic block diagram of an acoustic image generation apparatus (photoacoustic image generation apparatus) according to a second embodiment, illustrating the configuration thereof.

Second Embodiment of Acoustic Image Generation Apparatus and Progress Display Method A second embodiment of the present invention will be described next. FIG. 14 is a block diagram of a photoacoustic image generation apparatus according to the second embodiment, illustrating the configuration thereof. The present embodiment differs from the first embodiment in that it uses an acceleration sensor as the coordinate obtaining means. Therefore, the detailed description of the components identical to those of the first embodiment is omitted unless otherwise specifically required.

The photoacoustic image generation apparatus 10 of the present embodiment includes an ultrasonic probe (probe) 11, an ultrasonic unit 12, a laser unit 13, an image display means 14, a coordinate obtaining means 15 and 42a, and an input means 16.

<Coordinate Obtaining Means>

In the present embodiment, the coordinate obtaining means is an acceleration sensor unit which is constituted by the coordinate information obtaining section 15 and the acceleration sensor 42a. The acceleration sensor unit may measure a relative coordinate from a reference point based on acceleration and an angular velocity detected by the acceleration sensor 42a. As for the acceleration sensor 42a, for example, a three-axis acceleration sensor or a six-axis motion sensor may be used. The three-axis acceleration sensor is a sensor that detects three-axis components (Ax, Ay, Az) of acceleration and measures translational motion of an object. The six-axis motion sensor is a sensor that simultaneously detects three-axis components (Ax, Ay, Az) of acceleration and three-axis components ($\omega x$, $\omega y$, $\omega z$) of angular velocity and simultaneously measures translational motion and rotational motion of an object. In these sensors, the three-axis components (Ax, Ay, Az) of acceleration are detected from inertial force generated when acceleration is applied to a mass based on the law of Newton, while the three-axis components ($\omega x$, $\omega y$, $\omega z$) of angular velocity are detected from Coriolis force generated when angular velocity is applied to a mass based on the law of Coriolis. According to the acceleration sensor unit, the magnetic field generation section for defining the absolute coordinate as in the first embodiment is unnecessary and the configuration of the apparatus is simplified. Then, the coordinate information obtaining section 15 calculates a coordinate from a value measured by the acceleration sensor unit in the present embodiment and sends the coordinate information to the ultrasonic unit 12.

<Ultrasonic Unit>

The target scanning length is set by the scanning length setting means 45 in the same manner as in the first embodiment. That is, the target scanning length may be set by setting a numerical value arbitrarily inputted by the user, by setting a numerical value selected from predetermined candidates, or by specifying a range to be actually scanned using the switch 44a for setting scanning length. Also, the scanned length is calculated by the scanned length calculation means 46 in the same manner as in the first embodiment. In the present embodiment, a current relative coordinate of the probe 11 with reference to the probe 11 at the scanning start point is obtained by the acceleration sensor unit and the scanned length is calculated based on the relative coordinate. For example, if the probe is scanned only by the translational motion, a relative travel distance obtained through integration of the three-axis components of acceleration itself is the scanned length.

Also, according to the acoustic image generation apparatus of the present embodiment, it is possible, in a scanning process in which a probe having an ultrasonic transducer is scanned in generating an acoustic image, to sequentially obtain a coordinate of the probe in real space, calculate a scanned length based on the sequentially obtained coordinate, and generate a progress level display that displays progress of the scanning process based on the Predetermined target scanning length and the scanned length. Thus, the present embodiment may provide identical advantageous effects to those of the first embodiment.

Figure 15:
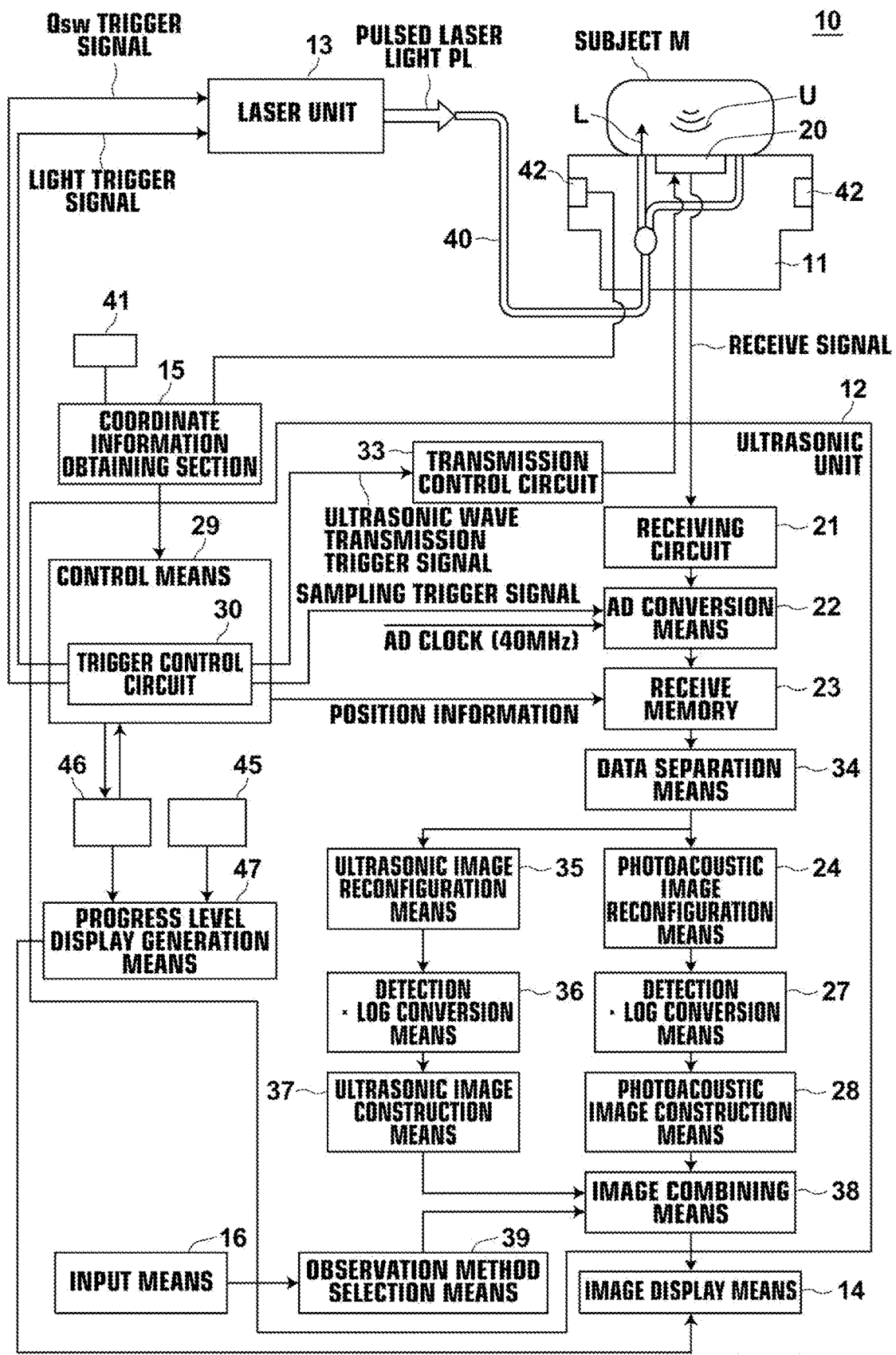
FIG. 15 is a schematic block diagram of an acoustic image generation apparatus (photoacoustic image generation apparatus) according to a third embodiment, illustrating the configuration thereof.

Third Embodiment of Acoustic Image Generation Apparatus and Progress Display Method Next, a third embodiment of the acoustic image generation apparatus and the progress display method of the present invention will be described in detail. FIG. 15 is a block diagram of an acoustic image generation apparatus according to the third embodiment, illustrating the configuration thereof. The present embodiment differs from the first embodiment in that it generates an ultrasonic image as a reflected acoustic wave image, in addition to a photoacoustic image. Therefore, the detailed description of the components identical to those of the first embodiment is omitted unless otherwise specifically required.

The photoacoustic image generation apparatus 10 of the present embodiment includes an ultrasonic probe (probe) 11, an ultrasonic unit 12, a laser unit 13, an image display means 14, a coordinate obtaining means 15, 41, and 42, and an input means 16, as in the first embodiment.

<Ultrasonic Unit>

The ultrasonic unit 12 of the present embodiment further includes a transmission control circuit 33, a data separation means 34, an ultrasonic image reconfiguration means 35, a detection•log conversion means 36, and an ultrasonic image construction means 37 in addition to the components of the photoacoustic image generation apparatus shown in FIG. 1. In the present embodiment, the receiving circuit 21, AD conversion means 22, receive memory 23, ultrasonic image reconfiguration means 24, detection•log conversion means 27, photoacoustic image construction means 28, ultrasonic image reconfiguration means 35, detection•log conversion means 36, and ultrasonic image construction means 37 correspond, as a unit, to the acoustic image generation means of the present invention.

In the present embodiment, the probe 11 performs outputting (transmission) of an ultrasonic wave to a subject and detection (reception) of a reflected ultrasonic wave (reflected acoustic wave) of the transmitted ultrasonic wave from the subject, in addition to the detection of a photoacoustic signal. As for the ultrasonic transducer that performs transmission and reception of ultrasonic waves, the ultrasonic transducer of the present invention may be used or a new transducer for transmission and reception of ultrasonic waves provided separately in the probe 11 may be used. Further, the transmission and reception of the ultrasonic wave may be separated. For example, an ultrasonic wave may be transmitted from a position different from the probe 11 and a reflected ultrasonic wave of the transmitted ultrasonic wave may be received by the probe 11.

The trigger control circuit 30 sends an ultrasonic wave transmission trigger signal that instructs transmission of an ultrasonic wave to the transmission control circuit 33. In response to the trigger signal, the transmission control circuit 33 causes an ultrasonic wave to be transmitted from the probe 11. After the transmission of the ultrasonic wave, the probe 11 detects a reflected ultrasonic wave from the subject.

The reflected ultrasonic wave detected by the probe 11 is inputted to the AD conversion means 22 via the receiving circuit 21. The trigger control circuit 30 sends a sampling trigger signal to the AD conversion means 22 in conjunction with the transmission timing of the ultrasonic wave to cause the sampling of the reflected ultrasonic wave to be started. Here, whereas the reflected ultrasonic wave reciprocates between the probe 11 and the ultrasonic wave reflection point, the photoacoustic signal travels one way from the point of generation to the probe 11. As the detection of reflected ultrasonic wave takes twice as long as the detection of a photoacoustic signal generated at the same depth, the sampling clock of the AD conversion means 22 may be reduced to half that of the photoacoustic signal sampling, for example, 20 MHz. The AD conversion means 22 stored a sampled signal of reflected ultrasonic wave in the receive memory 23. Either the sampling of photoacoustic signal or the sampling of reflected ultrasonic wave may precede the other.

The data separation means 34 separates the sampled signal of photoacoustic image from the sampled signal of reflected ultrasonic wave stored in the receive memory 23. The data separation means 34 inputs the separated sampled signal of photoacoustic image to the photoacoustic image reconfiguration means 24. The generation of a photoacoustic image is performed in the same manner as in the first embodiment. In the mean time, the data separation means 34 inputs the separated sampled signal of reflected ultrasonic wave to the ultrasonic image reconfiguration means 35.

The ultrasonic image reconfiguration means 35 generates data of each line of an ultrasonic image based on the reflected ultrasonic waves (sampled signals thereof) detected by a plurality of transducers of the probe 11. For the generation of data of each line, the delay-and-sum method and the like may be used as in the generation of data of each line in the photoacoustic image reconfiguration means 24. The detection•log conversion means 36 obtains an envelope of the data of each line outputted from the ultrasonic image reconfiguration means 35 and performs log conversion on the obtained envelope.

The ultrasonic image construction means 37 constructs an ultrasonic image based on the log-converted data of each line.

The image combining means 38 combines the photoacoustic image and the ultrasonic image. For example, the image combining means 38 combines the photoacoustic image and the ultrasonic image by superimposition. The combined image is displayed on the image display means 14. It is also possible to display the photoacoustic image and the ultrasonic image on the image display means side-by-side or by switching.

In the present embodiment, the photoacoustic image generation apparatus generates an ultrasonic image in addition to a photoacoustic image. By referring to the ultrasonic image, a portion which cannot be imaged by the photoacoustic image may be observed.

INDUSTRIAL APPLICABILITY

In the foregoing, the description has been made of a case in which the acoustic mage generation apparatus of the present invention is applied to a photoacoustic image generation apparatus, but the present invention is not limited to this. For example, the present invention may also be applied to a conventional ultrasonic image generation apparatus without photoacoustic image generation function. As for such an acoustic image generation apparatus, for example, an apparatus formed by removing the laser unit, the light emitting means, and the like from the apparatus of the third embodiment may be employed.

What is claimed is:

1. An acoustic image generation apparatus, comprising:
a probe including:
an acoustic detection element that detects an acoustic wave propagating in a subject, and
a sensor;
an ultrasonic unit configured to:
generate, based on an acoustic signal of the acoustic wave detected by the acoustic detection element, an acoustic image of the acoustic signal;
set a target scanning length in a scanning process of the probe;
sequentially obtain a coordinate of the probe in real space by the sensor;
calculate a scanned length based on the coordinates obtained by the sensor; and
generate a progress level display that indicates progress of the scanning process based on the target scanning length and the scanned length; and
a display including a screen that displays the progress level display,
wherein the progress level display is a progress meter having a bar graph shape and including an indicator that indicates the progress level,
wherein the progress meter includes a scanning assist display that assists the scanning of the probe such that the scanning process is completed properly,
wherein the scanning assist display includes an ideal speed display that guides the scanning of the probe such that the scanning speed of the probe may be kept at a predetermined value,
wherein the ideal speed display is a constant speed index, the constant speed index moves above the progress meter at a constant speed in a forward direction of the indicator, and
wherein, in a case in which the distance between a position of the constant speed index and a position of the indicator becomes greater than or equal to a predetermined value, movement of the constant speed index is resumed at a position above the indicator.

2. The acoustic image generation apparatus as claimed in claim 1, wherein the scanning assist display includes a scanning limit display that indicates a position above the progress meter that corresponds to an upper limit of a movement amount of the probe, such that the scanning speed of the probe is within a predetermined range.

3. The acoustic image generation apparatus as claimed in claim 1, wherein the ultrasonic unit is further configured to calculate a coordinate of a pixel included in an imaging area defined by the probe and located remote from the center axis of the probe in the real space based on the coordinate of the probe in the real space, and calculates the scanned length based on the coordinate of the pixel in the real space.

4. The acoustic image generation apparatus as claimed in claim 1, wherein the ultrasonic unit is further configured to terminate the generation of the acoustic image when a variation in the scanned length becomes greater than or equal to a predetermined value.

5. The acoustic image generation apparatus as claimed in claim 1, wherein the sensor is a magnetic sensor.

6. The acoustic image generation apparatus as claimed in claim 1, wherein the sensor is an acceleration sensor.

7. The acoustic image generation apparatus as claimed in claim 1, wherein:
the probe includes a light projector that projects measuring light onto the subject, and the acoustic detection element detects a photoacoustic wave generated in the subject due to the projection of the measuring light; and
the ultrasonic unit is further configured to generate a photoacoustic image based on a photoacoustic signal of the photoacoustic wave.

8. The acoustic image generation apparatus as claimed in claim 1, wherein:
the acoustic detection element detects a reflected acoustic wave of an acoustic wave transmitted to the subject; and
the ultrasonic unit is further configured to generate a reflected acoustic wave image based on a reflected acoustic wave signal of the reflected acoustic wave.

9. A progress display method, in a scanning process in which a probe including an acoustic detection element and a sensor is scanned in generating an acoustic image, the method comprising the steps of:

sequentially obtaining a coordinate of the probe in real space by the sensor;

calculating a scanned length based on the sequentially obtained coordinates;

generating a progress level display that indicates progress of the scanning process based on a predetermined target scanning length and the scanned length; and displaying the progress level display on a display, wherein the progress level display is a progress meter having a bar graph shape and including an indicator that indicates the progress level, wherein the progress meter includes a scanning assist display that assists the scanning of the probe such that the scanning process is completed properly, wherein the scanning assist display includes an ideal speed display that guides the scanning of the probe such that the scanning speed of the probe is kept at a predetermined value, wherein the ideal speed display is a constant speed index, the constant speed index moves above the progress meter at a constant speed in a forward direction of the indicator, and wherein, in a case in which the distance between a position of the constant speed index and a position of the indicator becomes greater than or equal to a predetermined value, movement of the constant speed index is resumed at a position above the indicator.

10. The progress display method as claimed in claim 9, wherein the scanning assist display includes a scanning limit display that guides the scanning of the probe such that the scanning speed of the probe falls within a predetermined range.

11. The progress display method as claimed in claim 9, wherein the scanned length is calculated by calculating a coordinate of a pixel included in an imaging area defined by the probe and located remove from the center axis of the probe in the real space based on the coordinates of the probe in the real space, and based on the coordinate of the pixel in the real space.

* * * * *